(12) United States Patent
Akiyama et al.

(10) Patent No.: US 8,224,600 B2
(45) Date of Patent: Jul. 17, 2012

(54) METHOD OF MONITORING DETERIORATION OF LUBRICATING OIL AND DEVICE THEREFORE

(75) Inventors: Yo Akiyama, Nagasaki-ken (JP);
Akihiko Yano, Nagasaki-ken (JP);
Junichi Kaga, Kanagawa-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 854 days.

(21) Appl. No.: 12/252,810

(22) Filed: Oct. 16, 2008

(65) Prior Publication Data
US 2009/0216471 A1    Aug. 27, 2009

(30) Foreign Application Priority Data
Feb. 22, 2008  (JP) ................. 2008-040845

(51) Int. Cl.
*G01R 27/00* (2006.01)
(52) U.S. Cl. ........................................................ 702/65
(58) Field of Classification Search ............... 702/65
See application file for complete search history.

(56) References Cited

U.S. PATENT DOCUMENTS

| | | | |
|---|---|---|---|
| 4,646,070 A | 2/1987 | Yasuhara et al. | |
| 5,067,455 A * | 11/1991 | Okajima et al. | 123/196 R |
| 5,540,086 A * | 7/1996 | Park et al. | 73/53.05 |
| 5,604,441 A | 2/1997 | Freese et al. | |
| 7,826,987 B2 * | 11/2010 | Aikawa | 702/50 |
| 2006/0114007 A1 * | 6/2006 | Cho | 324/698 |
| 2008/0027661 A1 * | 1/2008 | Aikawa | 702/50 |
| 2008/0272789 A1 * | 11/2008 | San Martin et al. | 324/355 |
| 2009/0315574 A1 * | 12/2009 | Akiyama et al. | 324/698 |
| 2010/0180671 A1 * | 7/2010 | Okuyama et al. | 73/53.05 |

FOREIGN PATENT DOCUMENTS

| | | |
|---|---|---|
| JP | 47-25383 Y1 | 8/1972 |
| JP | 58-85314 A | 5/1983 |
| JP | 58-128411 A | 8/1983 |
| JP | 60-13252 A | 1/1985 |
| JP | 3-227398 A | 10/1991 |
| JP | 10-078402 A | 3/1998 |
| JP | 11-316257 A | 11/1999 |
| JP | 2004-354082 A | 12/2004 |
| JP | 2006-177974 A | 7/2006 |
| JP | 2007-101237 A | 4/2007 |

OTHER PUBLICATIONS

Japanese Office Action issued in Japanese Patent Application No. 2008-040845 on Oct. 21, 2011.

* cited by examiner

*Primary Examiner* — Michael Nghiem
(74) *Attorney, Agent, or Firm* — Birch, Stewart, Kolasch & Birch, LLP

(57) ABSTRACT

A method of monitoring deterioration of lubricating oil and a device therefore capable of judging deterioration of the oil with high accuracy suppressing measurement error due to mixing of foreign matter in the oil. Correlation between relative permittivity and TBN (total base number) of the lubricating oil is obtained beforehand (step S1), electric current and voltage are measured (step S2) when high-frequency voltage is applied between a pair of electrodes located in an oil path in a gas engine, permittivity of the oil is detected (step S3) based on the measurement of current and voltage, TBN of the oil is obtained (step S4) from the correlation between relative permittivity and TBN, and deterioration of the oil is judged by the obtained value of TBN.

15 Claims, 10 Drawing Sheets

METHOD OF MONITORING DETERIORATION OF LUBRICATING OIL AND DEVICE THEREFORE

BACKGROUND OF THE INVENTION

1. Field of the Invention

The present invention relates to a method and device for detecting deterioration of lubricating oil circulating in a gas engine for driving an electric generator to lubricate sliding surfaces in the engine and monitoring the lubricating oil deterioration, specifically to those with which deterioration of oil can be detected in real time.

2. Description of the Related Art

Gas engines for driving electric generators have an oil tank and oil supply device to supply lubricating oil to rotating parts and sliding parts in order to secure smooth movement of the parts preventing abrasion of them. The lubricating oil accumulated in the oil tank is supplied through oil path via an oil filter and oil cooler to pistons, cylinders, bearings, etc. for lubrication and cooling of them and returned to the oil tank to be again supplied to the parts to be lubricated.

The lubricating oil is exposed at high temperature and experiences mechanical stress in the gas engine and deteriorates, that is, viscosity and purity decreases. Therefore, it is necessary to change periodically the lubricating oil to new oil. To judge timing of changing oil, it is important to monitor deteriorated condition of the lubricating oil.

Conventionally, a method of judging degree of oil deterioration by periodically sampling lubricating oil from the engine and chemically analyzing the sample oil has been prevailed. However, considerable time is needed to obtain chemical analysis after sampling the lubricating oil, and it is hard to say changing oil has been done at proper timing. So, it has been demanded to develop a device able to detect deterioration of lubricating oil in real time.

A device for detecting deterioration of engine oil is disclosed in Document 1 (Japanese Laid-Open Patent Application No. 10-78402), with which change in electric property of oil due to deterioration is detected. According to the disclosure, a resistance sensor is provided in the oil sump of the engine to measure electric resistance of oil, and need of changing oil is informed to the operator when detected electric resistance of oil decreases to a prescribed value.

In Document 2 (Japanese Laid-Open Patent Application No. 2004-354082) is disclosed another example of device for detecting deterioration of engine oil. According to this invention, sensor for detecting oil deterioration is located in a main gallery where lubricating oil filtered via an oil filter passes to be supplied to sliding parts in the engine.

The oil deterioration detecting sensor is composed to have two electrodes facing each other with a certain distance to form a gap between the electrodes to constitute a condenser with lubricating oil flowing through the gap between the electrodes. Electric capacitance between the electrodes is measured by applying alternating voltage, and degree of deterioration is determined based on relative permittivity obtained from the measured electric capacitance.

However, with the art disclosed in the Document 1, degree of oil deterioration is judged based on decrease in electric resistance of the oil, which is susceptible to mixing of foreign matter such as carbon in the oil.

With the art disclosed in the Document 1, also the electric capacitance is influenced by temperature of the oil and foreign matter mixed in the oil, resulting in increased measurement deviation.

There are other methods of detecting deterioration of oil, for example, by measuring change in viscosity, change in light transmission, or change in pH of the oil, however, these measurements are also influenced by temperature of the oil or foreign matter in the oil, and proper judgment of degree of deterioration of oil has been not easy.

SUMMARY OF THE INVENTION

The present invention was made in light of the problems of the prior art mentioned above, and the object of the invention is to provide a method of monitoring deterioration of lubricating oil and a device therefore capable of judging deterioration of oil with high accuracy suppressing measurement errors due to mixing of foreign matted in the oil and variation of temperature of the oil to the minimum.

To attain the object, the present invention proposes a method of monitoring deterioration of lubricating oil supplied via an oil path to rotating and sliding parts of a gas engine for driving an electric generator, wherein correlation between relative permittivity and TBN (total base number) of the lubricating oil is obtained beforehand, a pair of electrodes is located in the oil path, high-frequency alternating voltage is applied between the electrodes, values of applied voltage and resulting electric current are measured, and relative permittivity of the oil is calculated based on the measured values of voltage and current, TBN of the oil is determined from the correlation between relative permittivity and TBN of the oil, and deterioration of the oil is judged based on the determined TBN.

According to the invention, deteriorated condition of lubricating oil can be judged in real time without stopping operation of the dynamo gas engine, appropriate timing of changing oil can be known, and unnecessary oil change operation can be evaded.

TBN (total base number) is used as an indicator of acid neutralizing capacity and cleanliness level of oil. TBN decreases as oil deteriorates. There is a correlation between relative permittivity and TBN of oil that relative permittivity of oil increases as TBN of oil decreases, i.e. as oil deteriorates. Therefore, by degree of deterioration of oil can be detected easily and accurately from correlation obtained beforehand between permittivity and TBN of concerned lubricating oil.

It is preferable to prescribe a permissible upper limit of relative permittivity of the lubricating oil corresponding to a permissible lower limit of TBN and alarm that the oil is deteriorated when detected relative permittivity reaches or exceeds the permissible upper limit of relative permittivity.

By this, appropriate timing of changing oil is informed and unnecessary changing of lubricating oil can be evaded.

The invention proposes a device for monitoring deterioration of lubricating oil supplied via an oil path to rotating and sliding parts of a gas engine for driving an electric generator, wherein the device comprises a pair of electrodes facing each other with a certain distance and located in the oil path, a high-frequency alternating power source for applying high-frequency voltage between the electrodes, an amperemeter for measuring electric current flowing between the electrodes, a voltmeter for measuring voltage between the electrodes, and a processing means for judging deterioration of oil based on measurement of the amperemeter and voltmeter, the processing means comprising a memory section for storing data of correlation between relative permittivity and TBN (total base number) of the lubricating oil, a relative permittivity calculating section for calculating relative permittivity of the oil from the measured values of voltage and current, and an oil deterioration judging section for judging deterioration of the oil from calculated relative permittivity based on the correlation between relative permittivity and TBN of the oil.

It is preferable that a permissible upper limit of relative permittivity of the lubricating oil is prescribed to correspond to a permissible lower limit of TBN, and an alarm device is provided which alarms that the oil is deteriorated when the calculated relative permittivity reaches or exceeds the permissible upper limit of relative permittivity.

It is also preferable that an ultrasonic transducer is connected to at least one of the pair of electrodes so that ultrasonic vibration excited by the transducer by applying voltage to the transducer intermittently is propagated to the electrode to which the transducer is connected and the electrode is cleaned by the ultrasonic vibration.

By this, foreign matter such as soot adhered to the electrodes is removed and stable measurement of permittivity of oil can be performed.

It is preferable that a member of high permittivity is attached to at least one of the pair of electrodes so that the member coves an electrode plane of the at least one of the electrodes with even thickness so that the lubricating oil flows between the member and the other electrode or between the members when the member is attached to both the electrodes.

Relative permittivity of lubricating oil is low, it is about 2, so it is not easy to detect permittivity of oil accurately.

By attaching the high permittivity member to at least one of the electrodes to increase permittivity detected by the condenser constituted by the pair of electrodes, the high permittivity member, and the oil between them, the detected permittivity is increased. Therefore, even when it is difficult or impossible to detect permittivity of oil accurately, permittivity increased by attaching high permittivity member to the electrode can be detected and by subtracting offset value, i.e. value of permittivity increased due to the high permittivity member from the detected permittivity, permittivity of the oil can be obtained. Therefore, relative permittivity of oil can be detected with high accuracy.

It is also preferable that a member having high permittivity and able to generate ultrasonic vibration is attached to at least one of the pair of electrodes so that the member covers an electrode plane of the at least one of the electrodes with even thickness so that the lubricating oil flows between the member and the other electrode or between the members when the member is attached to both the electrodes.

With the construction, permittivity of oil can be detected with high accuracy because the member having high permittivity is attached to compose an electrode together with the existing electrode, and when foreign matter such as iron particle, carbon, etc. mixed in the oil accumulates in the gap between the electrodes, short-circuit occurs between the electrodes via the foreign matter and the member to allow the member to be energized by alternating voltage and the electrode is vibrated at ultrasound frequency by inverse piezoelectric effect (electrostrictive effect) occurred to the member 64. v As a result, foreign matter clogging the gap between the electrodes is removed by ultrasonic cleaning. Therefore, cleaning of the electrodes is performed accordingly when the gap between the electrodes is short-circuited, without the need of periodical switching behavior to perform cleaning of the electrodes.

It is also preferable to locate a temperature regulating means upstream of the pair of electrodes located in the oil path.

Resistivity of oil is sensitive to temperature of the oil. By regulating oil temperature to be at a prescribed temperature suitable for measurement of permittivity before the measurement is performed, more stable measurement of permittivity of oil can be performed without influenced by variation of oil temperature.

As has been describes heretofore, according to the invention, deterioration of lubricating oil can be detected in real time without stopping operation of engines. Therefore, appropriate timing for changing oil can be grasped and unnecessary changing of oil can be evaded.

DETAILED DESCRIPTION OF THE INVENTION

Figure 1:
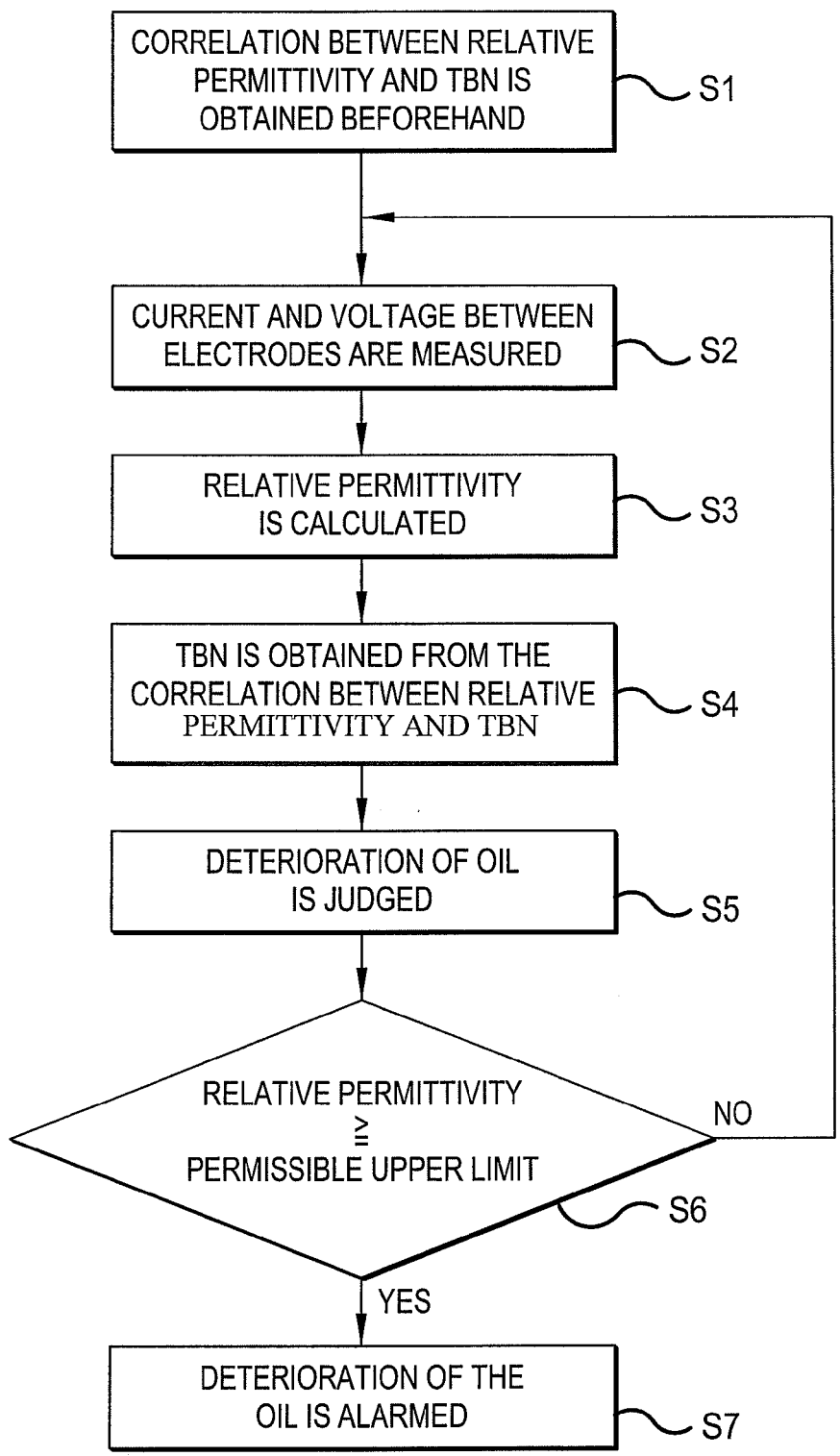
FIG. 1 is a flowchart of the first embodiment of the method of monitoring deterioration of lubricating oil according to the invention.

Embodiments of the present invention will now be detailed with reference to the accompanying drawings. It is intended, however, that unless particularly specified, dimensions, materials, relative positions and so forth of the constituent parts in the embodiments shall be interpreted as illustrative only not as limitative of the scope of the present invention.

FIGS. 1 to 6 are drawings to explain the method of monitoring deterioration of lubricating oil and the device therefore of an embodiment according to the invention, FIGS. 7 to 11 are drawing to explain modifications of embodiment.

In a gas engine 26 for driving an electric generator 27, lubricating oil accumulated in an oil tank is supplied through oil path via an oil filter and oil cooler to pistons, cylinders, bearings, etc. for lubrication and cooling of them and returned to the oil tank to be again supplied to the parts to be lubricated. The device of the embodiment of the invention is for detecting oil deterioration of the lubricating oil passing the oil path to monitor oil deterioration. Configuration of the oil deterioration monitoring device of an embodiment of the invention will be explained referring to FIG. 3. In the drawing, a pair of electrodes 21, 22 is located in an oil path 11 which is for supplying lubricating oil 10 to parts to lubricate the parts. A high-frequency power source 23 and an amperemeter 24 are provided in series between the two electrodes 21, 22, and a voltmeter 25 is provided parallel to the power source 23.

High-frequency voltage is applied between the electrodes 21, 22, and relative permittivity is obtained from measurement result of the amperemeter 24 and the voltmeter 25. Deterioration of the oil 10 is judged by a signal processing section 31 based on the correlation between relative permittivity and TBN of the oil stored in a memory section 31a, and the result of the judgment of deterioration of the oil judged by the signal processing section 31 is sent to an alarm device 32.

The electrodes 21 and 22 are disposed to face each other, the shape of which is not limited, maybe plate electrodes or annular electrodes. Preferably, both the electrodes 21 and 22 are plates of the same dimension disposed parallel to each other with a distance of d to compose a parallel-plate capacitor, and the pair of electrodes is located in the oil path 11. When an oil filter is provided in the oil path 11, the pair of electrodes 21, 22 is preferably located downstream from the oil filter.

The amperemeter 24 and voltmeter 25 are ones capable of outputting instantaneous value.

The high-frequency power source 23 applies high-frequency alternating voltage. About high frequencies of the power source 23 is detailed later.

The signal processing section 31 is realized for example by a MPU (computing microprocessor unit), DSP (digital signal processor), or PC (personal computer), and calculation of relative permittivity (relative permittivity is the ratio of permittivity of the concerned substance to permittivity of vacuum) from the measurement of current and voltage and judging of deterioration of the oil 10 are performed by the signal processing device according to a computer program. The PC, etc. in the signal processing section 31 may be one which can be used also as a means for controlling totally or partly the dynamo gas engine which is equipped with the oil deterioration monitoring device.

The alarm device 32 may be one which sounds an alarm or allows a predetermined region of a display panel to blink or output a message that the oil 10 is deteriorated when it is judged that the oil 10 is deteriorated.

Figure 5:
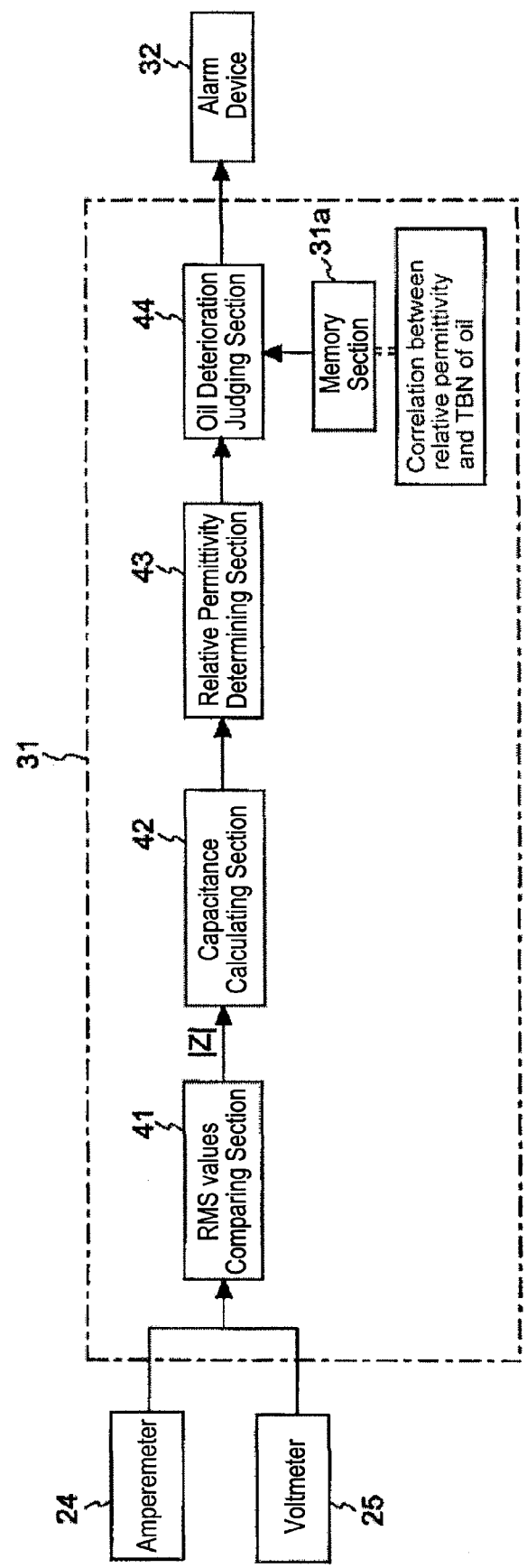
FIG. 5 is a block diagram of a signal processing section of the embodiment.
Figure 6:
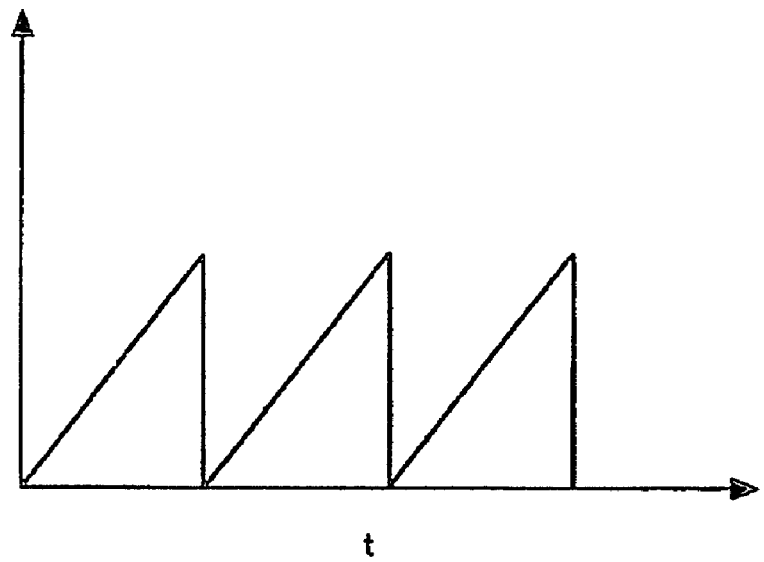
FIG. 6a is a graph showing an example of wave shape of alternating voltage.
FIG. 6b is a graph showing an example of result of Fourier analysis.
Figure 6:
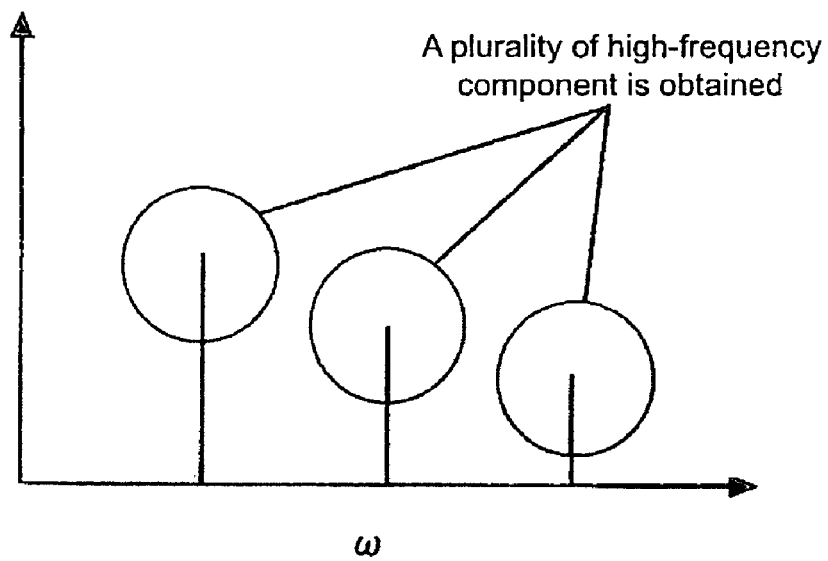

Next, signal processing and oil deterioration judging by the signal processing device 31 will be explained with reference to FIG. 5 showing a block diagram of the signal processing section of the embodiment. As shown in the drawing, the signal processing section 31 includes an RMS value comparing section 41, a capacitance calculating section 42, a relative permittivity determining section 43, an oil deterioration judging section 44, and a memory section 31a. These sections represent an arrangement in the computer program.

Current and voltage measured by the amperemeter 24 and voltmeter 25 are sent to the RMS values comparing section 41, where effective voltage and ampere are calculated and absolute value $|Z|$ of complex impedance Z, i.e. ($|Z|=|V|/|I|$) is calculated by comparing the effective voltage and effective ampere.

As high-frequency voltage is applied between the electrodes in the case of the embodiment, only capacitance value C is obtained from the reciprocal of the complex impedance $1/|Z|$ without taking into consideration of resistance R contained in the reciprocal of the complex impedance $1/|Z|$.

Relative permittivity e of the oil 10 is obtained from the capacitance value C in the relative permittivity determining section 43.

In the oil deterioration judging section 44, TBN of the oil 10 is obtained from a correlation between relative permittivity and TBN memorized beforehand in the memory section 31a, the correlation being inherent to the brand of oil, and oil deterioration is judged based on the obtained TBN value.

It is suitable to perform measurement by changing the frequency of the alternating voltage applied by the high-frequency power source 23 in a range of high frequencies. By measuring while varying the frequency of the alternating voltage, sensitivity of measuring relative permittivity e can be adjusted, and measuring of relative permittivity e can be performed at the most suitable frequency, resulting in increased accuracy of measurement.

For example, by performing preliminary experiment at a plurality of frequencies, frequency range can be confirmed at which sensitivity of measuring relative permittivity e is high and oil deterioration can be judged more appropriately.

Process flow in the method of monitoring oil deterioration according to the invention will be explained with reference to FIG. 1.

Figure 2:
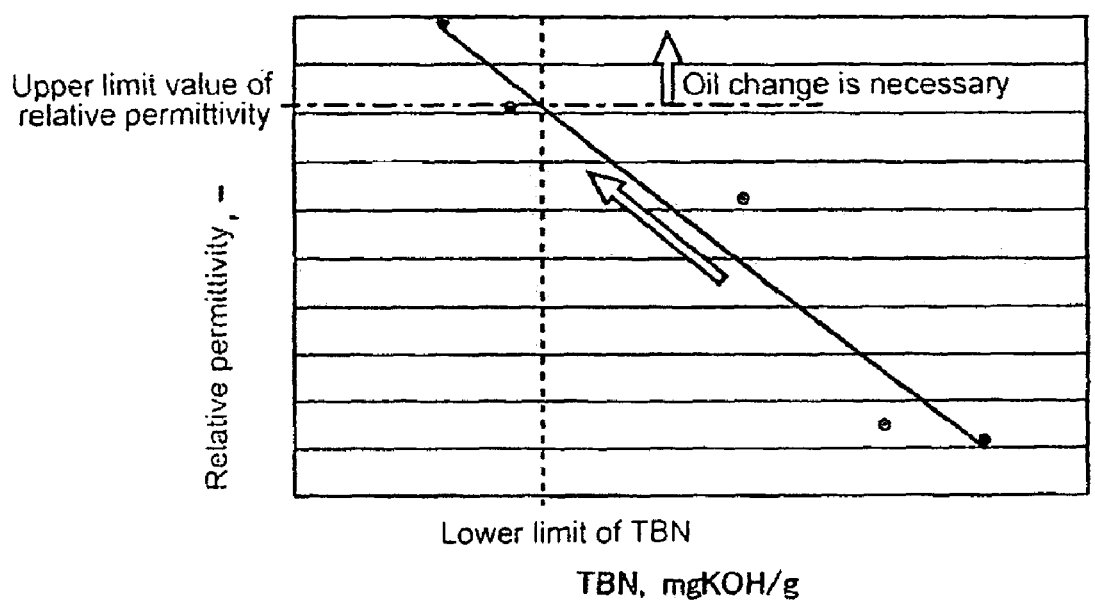
FIG. 2 is a graph showing an example of correlation between relative permittivity and TBN of oil.

Correlation between relative permittivity and TBN (total base number) of the lubricating oil used for the engine obtained beforehand is memorized at step S1. TBN is used as an indicator of deacidificating power and cleanliness level of oil. TBN decreases as oil deteriorates. There is a correlation between relative permittivity and TBN of oil that relative permittivity of oil increases as TBN of oil decreases as shown in FIG. 2. Correlation between relative permittivity and TBN of lubricating oil is different depending on kind or brand of lubricating oil, so it must be obtained beforehand for each kind or brand of oil by experiments.

Figure 3:
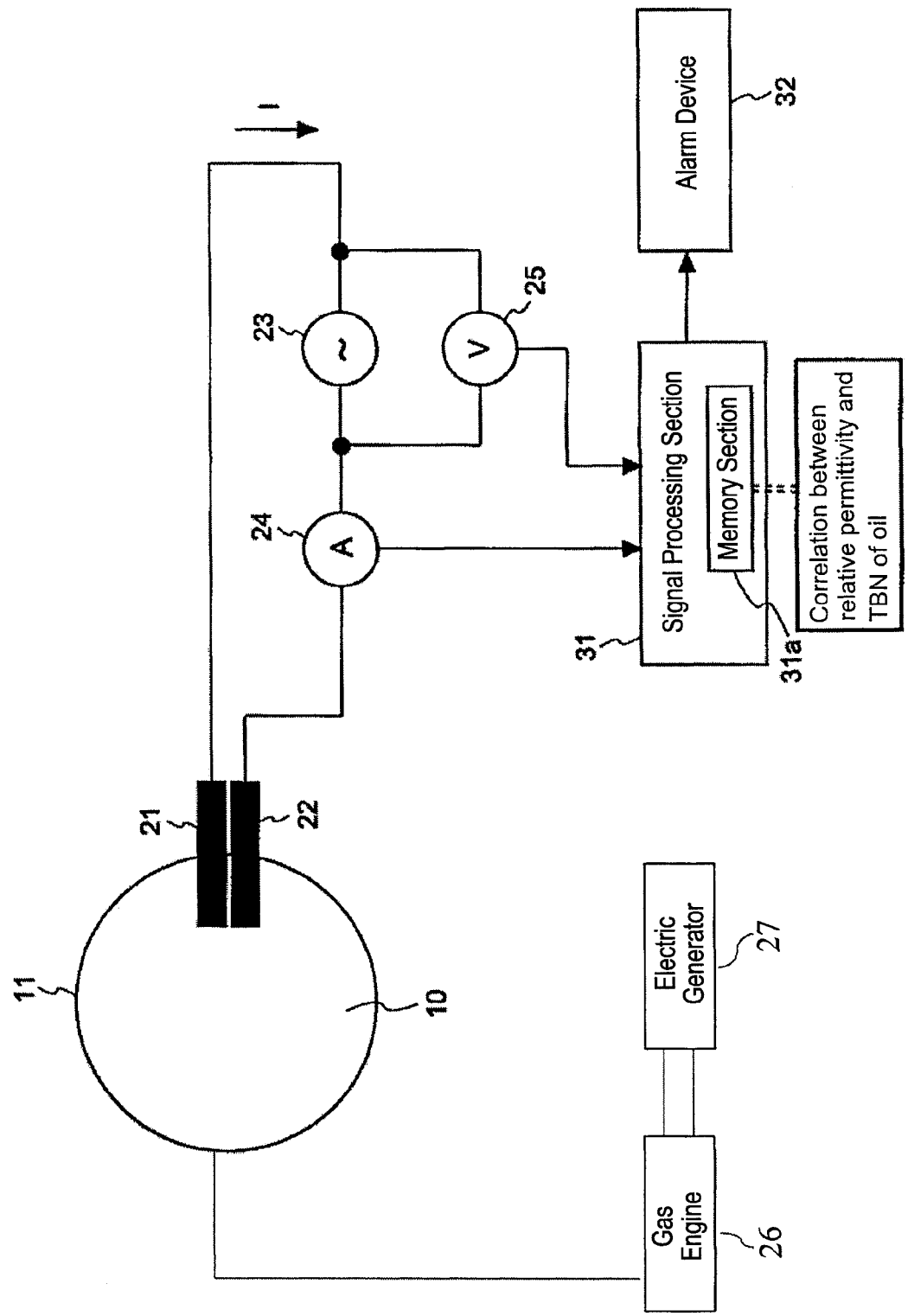
FIG. 3 is a drawing showing configuration of the oil deterioration monitoring device.
Figure 4:
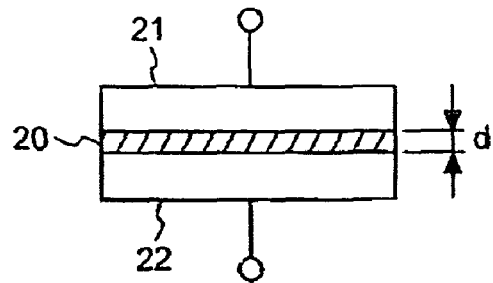
FIG. 4a is a cross sectional view of electrodes with oil layer shown hatched between the electrodes, the electrodes and oil layer constituting a parallel-plate capacitor for detecting relative permittivity of oil.
FIG. 4b is an electric circuit model of the parallel-plate capacitor.
FIG. 4c is a graph for explaining complex impedance of the circuit in a complex plane.
Figure 4:
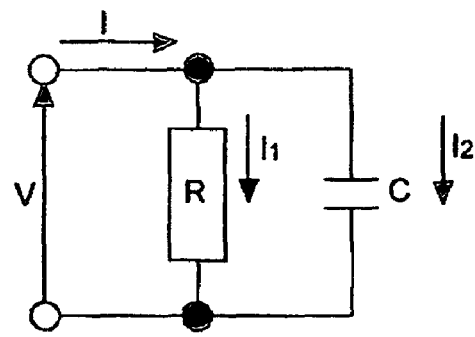
Figure 4:
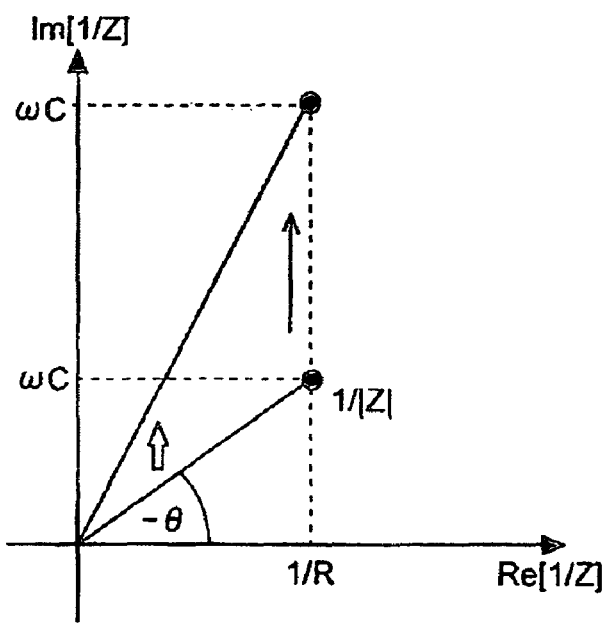

High-frequency voltage is applied between the electrodes 21, 22 by the high-frequency power source 23 shown in FIG. 3 and electric current and voltage are measured by the amperemeter 24 and voltmeter 25 at step S2. Relative permittivity is calculated based on the detected values of ampere and voltage in the signal processing section 31 at step S3. About calculation of relative permittivity will be detailed later. Current and voltage may be measured continuously or intermittently, preferably measured continuously.

TBN of oil is obtained from the correlation between relative permittivity and TBN of the concerned lubricating oil stored in the memory section 31a at step S4. Deteriorated condition of the oil is judged based on the obtained TBN at step S5.

A permissible upper limit value of relative permittivity is predetermined to correspond to a permissible lower limit of TBN which represents degree of deterioration of lubricating oil, as shown in FIG. 2 showing correlation between relative permittivity and TBN of the lubricating oil. The detected relative permittivity is compared with the limit value of relative permittivity at step S6. When the detected relative permittivity is equal to or larger that the prescribed limit value of relative permittivity, it is alarmed that the oil is deteriorated by the alarm device 32 at step S7.

As has been described, TBN decreases as the lubricating oil deteriorates, and relative permittivity increases as TBN decreases, so by determining a permissible upper limit value of relative permittivity corresponding to a permissible lower limit value of TBN for judging that the oil is deteriorated and alarming that the oil is deteriorated when the detected relative permittivity reaches or exceeds the upper limit value of relative permittivity, appropriate time of changing oil can be known exactly.

Next, measurement principle in the oil deterioration monitoring device of the embodiment will be explained.

An electric circuit model of a parallel-plate capacitor composed of electrode plates 21 and 22 facing with each other with a distance of d with lubricating oil layer 20 between the electrodes 21, 22 shown in FIG. 4a is assumed to be composed of resistance R and capacitance C connected in parallel as shown in FIG. 4b.

Assuming electric current of I ampere flows in the circuit when electric pressure of V volt is applied between the electrodes by the AC power source 23 at frequency of ω, and assuming the current flowing via the resistance of R ohm is I1 ampere and that flowing via the capacitance C farad is I2 ampere, the following equations are made true.

$$I = I1 + I2 \quad (1)$$

$$V = R \cdot I1 \quad (2)$$

$$V = (1/j\omega C) \cdot I2 \quad (3).$$

From equations (1) to (3), complex impedance. Z of the circuit is obtained from the following equation (4).

$$\begin{aligned} Z &= V/I \\ &= V/((1/R) + j\omega C) \cdot V) \\ &= 1/((1/R) + j\omega C)) \end{aligned} \quad (4)$$

The complex impedance Z can be represented in a complex plane as shown in FIG. 4c. In the graph of FIG. 4c, abscissa represents real part Re[1/Z] of reciprocal of complex impedance, and coordinate represents imaginary part Im[1/Z] of reciprocal of complex impedance, and reciprocal 1/Z is plotted on the graph. Direct distance from the origin to the plotted point is the amplitude, i.e. absolute value 1/|Z| of reciprocal of absolute |Z| of the complex impedance Z, and angle θ is the argument of reciprocal 1/Z of the complex impedance Z.

As shown in FIG. 4c, real part of reciprocal 1/Z corresponds to reciprocal 1/R of resistance component R and imaginary part of reciprocal 1/Z corresponds to capacitance component ωC. So, when reciprocal 1/|Z| and argument θ are obtained, value of resistance R and capacitance C can be obtained. Electric conductivity σ and relative permittivity ε of the oil layer 20 between the electrodes 21, 22 can be obtained from the detected value of resistance R and capacitance C using area S of the planar electrode and distance d between the electrodes.

Resistance R of the oil layer 20 varies depending on deteriorated condition, temperature, kind of base oil, etc. of the lubricating oil, and to make the influence of resistance R negligible when calculating complex impedance Z from the equation (4), high-frequency voltage is applied between the electrodes. By increasing ω in the equation (4), the second term in the denominator increases and the first term, i.e. Resistance component R becomes negligible for approximation. By sufficiently increasing frequency ω of voltage applied between the electrodes, capacitance component ωC increases so that reciprocal of resistance component 1/R is negligible as compared with the capacitance component ωC, the electric circuit model can be assumed to include only capacitance C.

In that case, argument θ is π/2, so measurement of argument θ is unnecessary.

It is preferable that frequency of alternating voltage applied between the electrodes is such that the real part (1/R) of reciprocal 1/Z of complex impedance Z becomes equal to or smaller than 1/100 times the imaginary part (jωC) thereof.

As to waveform of the alternating voltage, sinusoidal wave, rectangular wave, saw-tooth wave, and inversed saw-tooth wave can be suitably adopted. When waveform other than sinusoidal wave, for example, saw-tooth wave as shown in FIG. 6a is adopted, Fourier's analysis of obtained impedance as function of time gives a plurality of high-frequency components of integral multiple of fundamental frequency of the waveform as shown in FIG. 6b. Therefore, by determining relative permittivity using complex impedance for each of high-frequency components, relative permittivity can be obtained for a plurality of frequencies. That is, by applying high-frequency alternating voltage of waveform of rectangular, saw-tooth, or inversed saw-tooth wave to apply between the electrodes, complex impedance can be obtained for a plurality frequencies and frequency most appropriate to detect relative permittivity can be found by a single measurement. Moreover, by using a plurality relative permittivity obtained for a plurality of frequencies to determine TBN of the oil to judge oil deterioration, more reliable judgment of oil deterioration is made possible.

The First Modification of the Embodiment

Figure 7:
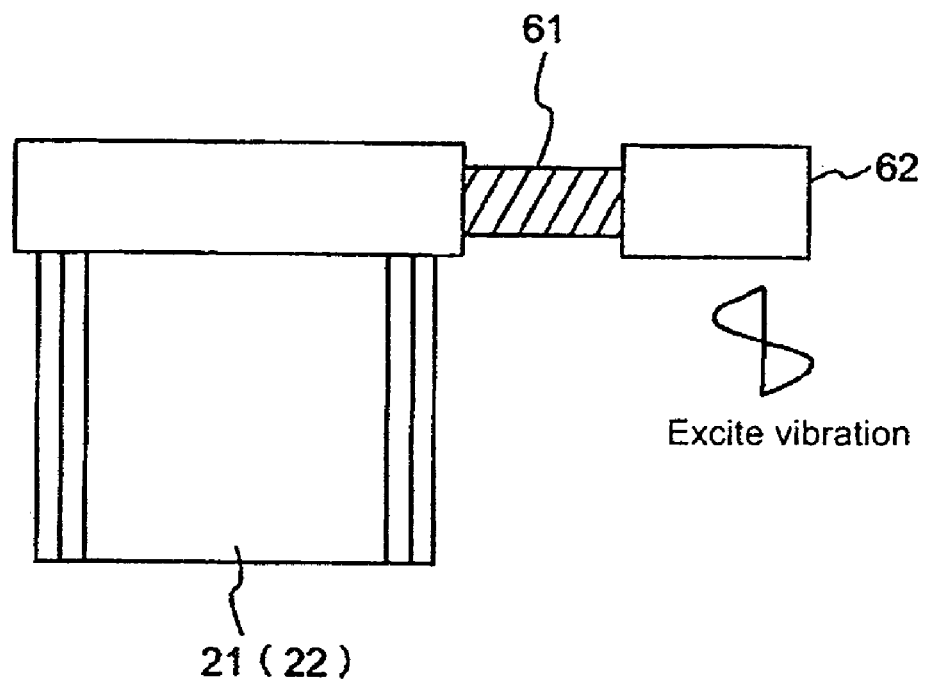
FIG. 7 is a drawing showing a configuration of electrodes of the first modification provided with, a self cleaning means.

In FIG. 7 is shown a configuration of a pair of electrodes of a first modification provided with a self cleaning means.

As shown in the drawing, an ultrasonic transducer 61 is connected to at least one of the electrodes 21, 22, and a weight 62 is attached to the ultrasonic transducer 61 at a side opposite to the side thereof connecting to the electrode. It is preferable to attach the ultrasonic transducer 61 to each of the electrodes 21, 22 so that both the electrodes can be cleaned by ultrasonic cleaning.

The ultrasonic transducer 61 is a device to convert electric energy to ultrasonic mechanical vibration. An electrostrictive vibrator or magnetostrictive vibrator can be used as the ultrasonic transducer 61; however, it is preferable to use a piezoelectric element device.

By applying voltage to the ultrasonic transducer 61 while stopping permittivity measuring, the electrode(s) 21(22) is vibrated by the ultrasonic transducer 61 and foreign matter such as soot, etc. adhering to the electrode(s) is removed.

The Second Modification of the Embodiment

Figure 8:
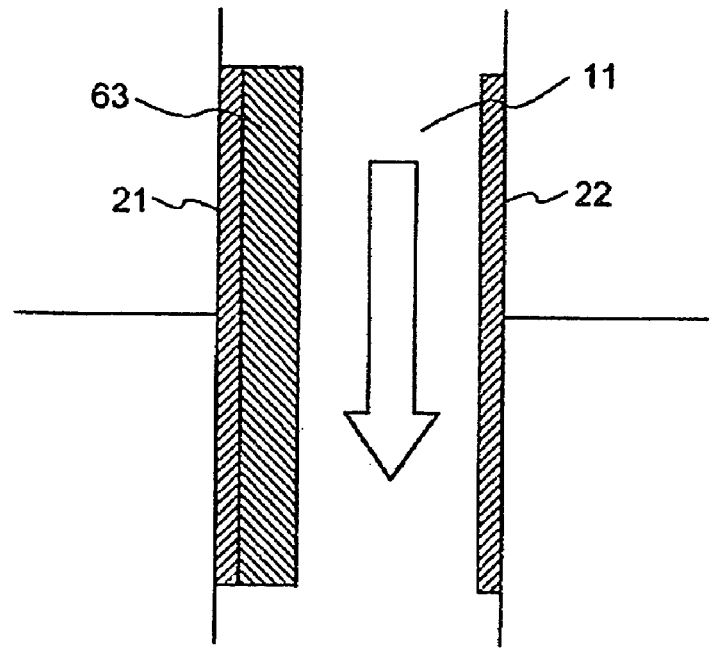
FIG. 8 is a drawing showing configuration of electrodes of the second modification provided with a permittivity offsetting means.

In FIG. 8 is shown a configuration of a pair of electrodes of the second modification provided with a permittivity offsetting means. In the embodiment, a member 63 of high permittivity is attached to at least one of the electrodes 21, 22, in the example of FIG. 8 the high permittivity member 63 is attached only to the electrode 21, so that capacitance of a condenser constituted by the electrodes 21, 22, and the high permittivity member 63 and oil flowing between the high permittivity member 63 and electrode 22 increases. The high permittivity member 63 is attached to the electrode plane so that it is even in thickness along the platy electrode 21 to compose an electrode together with the electrode 21. Barium titanate (relative permittivity is about 1200), titanium dioxide (relative permittivity is about 100), is adopted for example as the high permittivity member.

Permittivity of the oil can be obtained by subtracting permittivity increment due to the high permittivity member 63 from measured permittivity.

Figure 9:
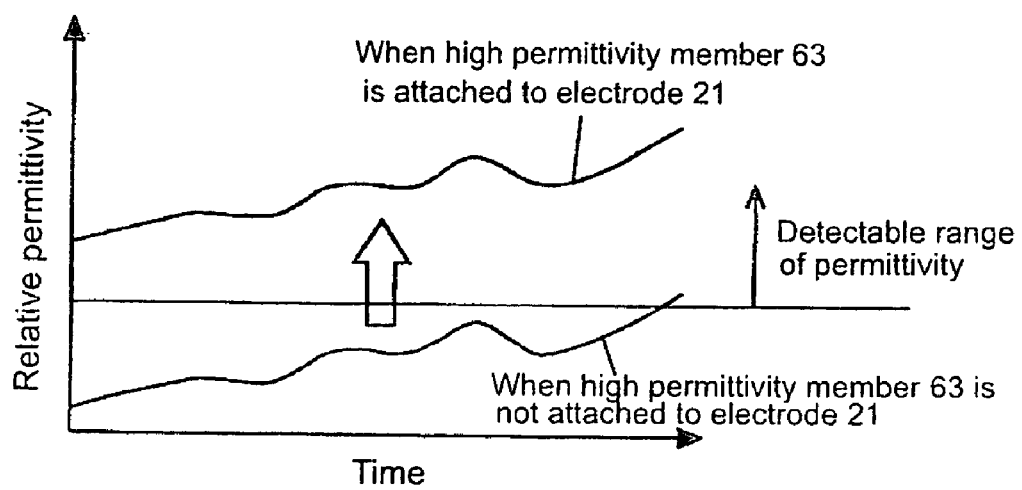
FIG. 9 is a graph showing results of measurement of permittivity when the electrode is provided with the permittivity offsetting means as shown in FIG. 8.
Figure 10:
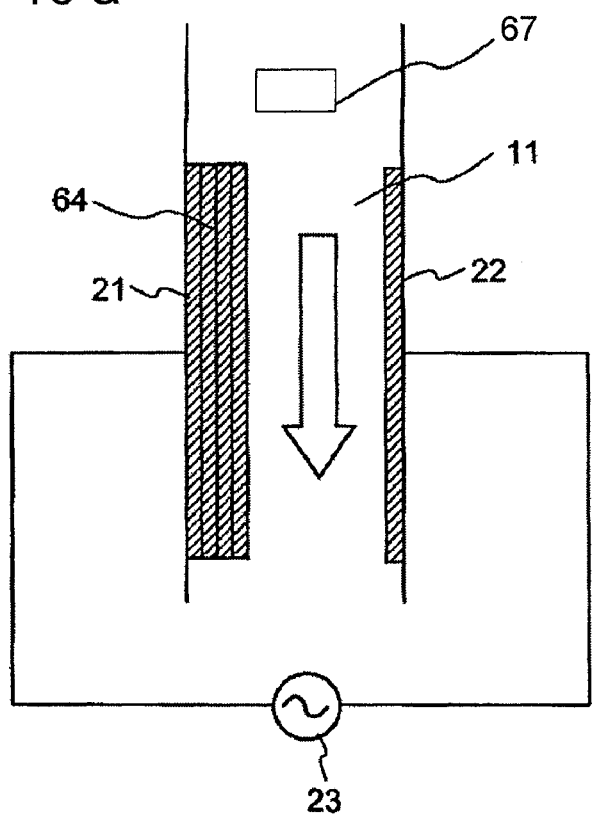
FIG. 10a is a drawing showing configuration of electrodes of the third modification provided with a combined self cleaning and permittivity offsetting means when oil is smoothly flowing through the gap between the electrodes.
FIG. 10b is when foreign matter clogs the gap.
Figure 10:
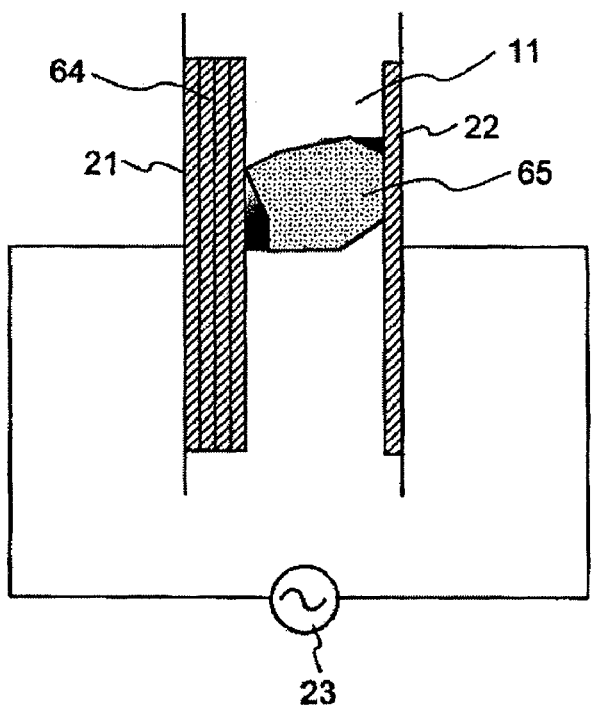

Relative permittivity of lubricating oil is low, which is about 2, so it is not easy to detect permittivity of oil accurately. By attaching the high permittivity member 63 to the electrode 21 as shown in FIG. 8 to increase permittivity detected by the condenser constituted by the electrodes 21, 22, high permittivity member 63, and the oil between them, the detected-permittivity is increased and detection of permittivity with a high degree of accuracy is achievable, i.e. is offset from detected permittivity without the high permittivity member, as shown in FIG. 9.

Therefore, even when it is difficult or impossible to detect permittivity of oil accurately, permittivity increased by attaching high permittivity member 63 to the electrode can be detected and by subtracting offset value, i.e. value of permittivity increased due to the high permittivity member 63 from the detected permittivity, permittivity of the oil can be obtained. Therefore, relative permittivity of oil can be detected with high accuracy.

The Third Modification of the Embodiment

In FIG. 10*a* and 10*b* are shown a configuration of electrodes of the third modification provided with a combined self cleaning and permittivity offsetting means. FIG. 10*b* shows when foreign matter 65 clogs the gap between the electrodes.

In the embodiment, a member 64 having high permittivity and able to generate ultrasonic vibration is attached to at least one of the electrodes 21, 22. In the example of FIG. 10*a*, the member 64 is attached only to the electrode 21. As the member 64 is adopted preferably lead zirconate titanate (PZT), etc., for example. The member 64 is attached to the electrode plane so that it is even in thickness along the platy electrode 21 to compose an electrode together with the electrode 21. The member 64 may be composed as a laminated member consisting of a plurality of thin plates.

According to the embodiment, permittivity of oil can be detected with high accuracy because the member 64 having high permittivity is attached to the electrode 21 to compose an electrode, and when foreign matter 65 such as iron powder, carbon, etc. mixed in the oil accumulates in the gap between the electrode composed of the electrode 21 and the member 64 and the electrode 22, short-circuit occurs between the electrodes 21, 22 via the foreign matter and the member 64 to allow the member 64 to be energized by alternating voltage and the electrode 21 is vibrated at ultrasound frequency by inverse piezoelectric effect (electrostrictive effect) occurred to the member 64. As a result, foreign matter 65 clogging the gap between the electrodes is removed by ultrasonic cleaning.

Therefore, cleaning of the electrodes is performed accordingly when the gap between the electrodes is short-circuited, without the need of periodical switching behavior to perform cleaning of the electrodes.

The Fourth Modification of the Embodiment

Figure 11:
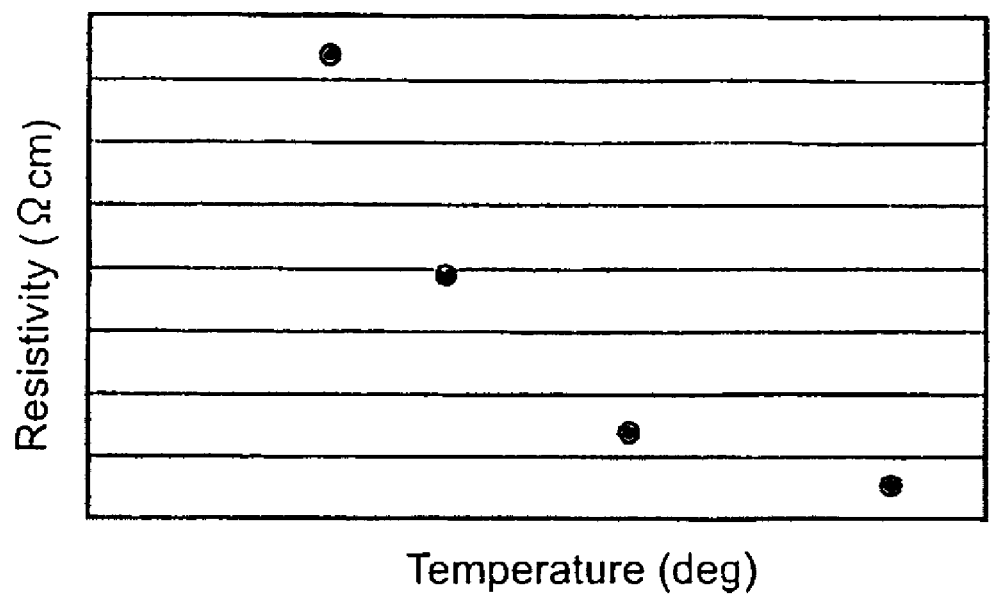
FIG. 11 is a graph showing electric resistance vs temperature of oil.

A fourth embodiment of the device according to the invention is composed such that a temperature regulator 67 (see FIG. 10*a*) is provided upstream of the electrode in the oil path so that oil temperature flowing through the gap between the electrodes is controlled to a prescribed temperature. Resistivity of oil is sensitive to temperature as shown in FIG. 11. So, by controlling temperature of lubricating oil flowing through the gap between the electrodes to a temperature proper for measurement of capacitance C of the condenser composed by the electrodes 21, 22 and oil in the gap between the electrodes before the measurement is performed, more stable measurement of permittivity of the oil can be performed without influenced by variation of oil temperature.

With the method of monitoring deterioration of lubricating oil and the device therefore, measurement error of permittivity of oil due to mixing foreign matted in the oil is suppressed to the minimum and more accurate judgment of oil deterioration can be obtained. The method and device can be favorably applied to gas engines for driving electric generators to prevent wear of component parts secure smooth operation thereof.

By applying the method of monitoring deterioration of lubricating oil and the device therefore according to the invention to gas engines for driving electric generators, deterioration of lubricating oil can be detected in real time without stopping operation of the engines. Therefore, appropriate timing for changing oil can be grasped and unnecessary changing of oil can be evaded.

The invention claimed is:

1. A method of monitoring deterioration of lubricating oil supplied via an oil path to rotating and sliding parts of a gas engine for driving an electric generator, the method comprising:

obtaining and storing, beforehand, a predetermined correlation between relative permittivity and TBN (total base number) of the lubricating oil;

applying high-frequency alternating voltage between a pair of electrodes located in the oil path;

measuring values of applied voltage and resulting electric current;

calculating relative permittivity of the oil based on the measured values of voltage and current;

determining an actual TBN of the oil from the predetermined correlation between relative permittivity and TBN of the oil; and judging deterioration of the oil based on the determined actual TBN, wherein a permissible upper limit of relative permittivity of the lubricating oil is prescribed to correspond to a permissible lower limit of TBN, and that the oil is deteriorated is alarmed when detected relative permittivity reaches or exceeds the permissible upper limit of relative permittivity.

2. A device for monitoring deterioration of lubricating oil supplied via an oil path to rotating and sliding parts of a gas engine for driving an electric generator, comprising:

a pair of electrodes facing each other with a certain distance and located in the oil path;

a high-frequency alternating power source for applying high-frequency voltage between the electrodes;

an amperemeter for measuring electric current flowing between the electrodes;

a voltmeter for measuring voltage between the electrodes; and processing means for judging deterioration of oil based on measurement of the amperemeter and voltmeter, the processing means including a memory section for storing data of predetermined correlation between relative permittivity and TBN (total base number) of the lubricating oil, a relative permittivity calculating section for calculating an actual relative permittivity of the oil from the measured values of voltage and current, and an oil deterioration judging section for judging deterioration of the oil from the calculated actual relative permittivity based on the predetermined correlation between relative permittivity and TBN of the oil, wherein a permissible upper limit of relative permittivity of the lubricating oil is prescribed to correspond to a permissible lower limit of TBN, and an alarm device is provided which alarms that the oil is deteriorated when the calculated relative permittivity reaches or exceeds the permissible upper limit of relative permittivity.

3. A device for monitoring deterioration of lubricating oil according to claim 2, wherein a first member having high permittivity and able to generate ultrasonic vibration is attached only to one of the pair of electrodes so that the first member covers an electrode plane of the one of the pair of electrodes with even thickness so that the lubricating oil flows between the first member and the other electrode or further to the first member being attached to the one of the pair of electrodes, a second member of high permittivity is attached to the other of the pair of electrodes so that the second member covers an electrode surface of the other of the pair of electrodes with even thickness so that the lubricating oil flows between the first and second members.

4. A device for monitoring deterioration of lubricating oil according to claim 3, wherein a temperature regulating means is located upstream of the pair of electrodes located in the oil path.

5. A device for monitoring deterioration of lubricating oil according to claim 2, wherein a temperature regulating means is located upstream of the pair of electrodes located in the oil path.

6. A device for monitoring deterioration of lubricating oil according to claim 2, wherein an ultrasonic transducer is connected to at least one of the pair of electrodes so that ultrasonic vibration produced by the transducer by applying voltage intermittently to the transducer is propagated to the electrode to which the transducer is connected and the electrode is cleaned by the ultrasonic vibration.

7. A device for monitoring deterioration of lubricating oil according to claim 2, wherein a first member of high permittivity is attached only to one of the pair of electrodes so that the first member covers an electrode plane of the one of the pair of electrodes with even thickness so that the lubricating oil flows between the first member and the other electrode or further to the first member being attached to the one of the pair of electrodes, a second member of high permittivity is attached to the other of the pair of electrodes so that the second member covers an electrode surface of the other of the pair of electrodes with even thickness so that the lubricating oil flows between the first and second members.

8. A device for monitoring deterioration of lubricating oil according to claim 2, wherein a temperature regulating means is located upstream of the pair of electrodes located in the oil path.

9. A device for monitoring deterioration of lubricating oil according to claim 2, wherein an ultrasonic transducer is connected to at least one of the pair of electrodes so that ultrasonic vibration produced by the transducer by applying voltage intermittently to the transducer is propagated to the electrode to which the transducer is connected and the electrode is cleaned by the ultrasonic vibration.

10. A device for monitoring deterioration of lubricating oil according to claim 9, wherein a first member of high permittivity is attached only to one of the pair of electrodes so that the first member covers an electrode plane of the one of the pair of electrodes with even thickness so that the lubricating oil flows between the first member and the other electrode or further to the first member being attached to the one of the pair of electrodes, a second member of high permittivity is attached to the other of the pair of electrodes so that the second member covers an electrode surface of the other of the pair of electrodes with even thickness so that the lubricating oil flows between the first and second members.

11. A device for monitoring deterioration of lubricating oil according to claim 9, wherein a first member having high permittivity and able to generate ultrasonic vibration is attached only to one of the pair of electrodes so that the first member covers an electrode plane of the one of the pair of electrodes with even thickness so that the lubricating oil flows between the first member and the other electrode or further to the first member being attached to the one of the pair of electrodes, a second member of high permittivity is attached to the other of the pair of electrodes so that the second member covers an electrode surface of the other of the pair of electrodes with even thickness so that the lubricating oil flows between the first and second members.

12. A device for monitoring deterioration of lubricating oil according to claim 9, wherein a temperature regulating means is located upstream of the pair of electrodes located in the oil path.

13. A device for monitoring deterioration of lubricating oil via an oil path to rotating and sliding parts of a gas engine for driving an electric generator, comprising:

a pair of electrodes facing each other with a certain distance and located in the oil path;

a high-frequency alternating power source for applying high-frequency voltage between the electrodes;

an amperemeter for measuring electric current flowing between the electrodes;

a voltmeter for measuring voltage between the electrodes; and processing means for judging deterioration of oil based on measurement of the amperemeter and voltmeter, the processing means including a memory section for storing data of predetermined correlation between relative permittivity and TBN (total base number) of the lubricating oil, a relative permittivity calculating section for calculating an actual relative permittivity of the oil from the measured values of voltage and current, and an oil deterioration judging section for judging deterioration of the oil from the calculated actual relative permittivity based on the predetermined correlation between relative permittivity and TBN of the oil, wherein a first member of high permittivity is attached only to one of the pair of electrodes so that the first member covers an electrode plane of the one of the pair of electrodes with even thickness so that the lubricating oil flows between the first member and the other electrode or further to the first member being attached to the one of the pair of electrodes, a second member of high permittivity is attached to the other of the pair of electrodes so that the second member covers an electrode surface of the other of the pair of electrodes with even thickness so that the lubricating oil flows between the first and second members.

14. A device for monitoring deterioration of lubricating oil according to claim 13, wherein at least one of the first and second members generates ultrasonic vibration.

15. A device for monitoring deterioration of lubricating oil according to claim 13, wherein a temperature regulating means is located upstream of the pair of electrodes located in the oil path.

* * * * *